United States Patent [19]

Boitiaux et al.

[11] Patent Number: 4,740,633

[45] Date of Patent: Apr. 26, 1988

[54] PROCESS FOR HYDROGENATING OLEFINS IN THE PRESENCE OF ETHERS

[75] Inventors: Jean-Paul Boitiaux, Poissy; Jean Cosyns, Maule; Michel Derrien, Rueil-Malmaison, all of France

[73] Assignee: Institut Francais du Petrole, Rueil-Malmaison, France

[21] Appl. No.: 885,889

[22] Filed: Jul. 15, 1986

[30] Foreign Application Priority Data

Jul. 15, 1985 [FR] France ................ 85 10919

[51] Int. Cl.$^4$ ................................ C07C 41/34
[52] U.S. Cl. ................................ 568/699
[58] Field of Search .......... 568/699, 697; 585/277

[56] References Cited

U.S. PATENT DOCUMENTS 3,489,778  1/1970  Van 't Hof .
4,447,653  5/1984  Vora ................................ 568/697
4,490,481 12/1984  Boitiaux et al. .

FOREIGN PATENT DOCUMENTS 1055233  1/1967  United Kingdom .

OTHER PUBLICATIONS

Mulik et al, CA 91:140251m, Osmov. Organ. Sintezi Neftekhimiya (Yaroslavl), 1978, (10), 24–7.
Compendium of Organic Synthetic Methods, Harrison et al, Wiley–Interscience (1971).

*Primary Examiner*—Howard T. Mars
*Attorney, Agent, or Firm*—Millen & White

[57] ABSTRACT

This process for hydrogenating an olefin contained in a mixture of said olefin with an ether and optionally with sulfur, comprises reacting hydrogen with said mixture in the presence of a noble metal-containing catalyst, said catalyst containing at least one first noble metal from the palladium, rhodium, iridium and platinum group and at least one second other metal from the gold and platinum group.

6 Claims, No Drawings

PROCESS FOR HYDROGENATING OLEFINS IN THE PRESENCE OF ETHERS

The present invention concerns a process for hydrogenating mixtures of ethers and olefins, optionally further containing traces of sulfur compounds. The hydrogenation may be partial or complete for a mixture of high olefinic hydrocarbons content or almost complete for a mixture of very high ether content to be purified.

BACKGROUND OF THE INVENTION

A large number of processes for converting hydrocarbons give olefins or olefin mixtures which still contain sulfur impurities. Examples of such processes are the pyrolysis processes such as steam-cracking, visbreaking, coking or catalytic cracking processes.

The so-produced olefins are often suitable for chemical uses but they may also be added to fuel or motor-fuel cuts. For these uses, the presence of olefins results in a number of disadvantages; for example, in motor-fuels, whereas olefins have a high Research octane number (F1), their Motor octane number (F2) on the contrary, is rather poor and requires, at least a partial hydrogenation of the concerned olefins to be improved.

The present generalized manufacture of lead-free gasoline requires the production of motor-fuels of higher octane number. One way of increasing the octane number is to react olefins with an alcohol such as, for example, as methanol, to produce the corresponding methyl-alkyl ethers. After etherification, the obtained cut generally contains, in addition to methyl-alkyl ethers, non-etherifiable olefins or olefins only etherifiable to a small extent and also sulfur compounds. The Research octane number of said cut is generally excellent but its Motor octane number is often too low. It may however be improved by partial hydrogenation of the olefins contained in the cut.

In the production of ethers for chemical and pharmaceutical uses, most of the processes use, as the starting material, the corresponding olefins, and the ethers obtained generally contain a small amount of unreacted olefins. The specifications in these uses prescribe a very thorough removal of these olefins so as to comply with very severe tests such as DENIGES test, for example, which requires an olefin content of the ether lower than 20 ppm. Accordingly, this requires a very extensive hydrogenation and hence a very high activity of the catalyst, which must be maintained even in the presence of traces of sulfur compounds.

The olefin hydrogenation techniques are already known and the metals from group VIII are excellent catalysts therefor. But, in the presence of sulfur compounds, it is observed that all these metals are deactivated and (or) poisoned more or less quickly. It is also possible to use metals from group VIII for purifying ethers by hydrogenation of the olefinic impurities. A French patent (No. 1,560,586) discloses such a technique where a nickel or cobalt catalyst is used. When using said technique, the hydrogenation is very effective in the absence of sulfur compounds but, to the contrary with a concentration of sulfur compounds of a few ppm, a more or less quick deactivation of the catalyst is observed. If the temperature is increased in order to compensate for this deactivation, the activity is increased to a certain extent but insufficiently and at the cost of a beginning degradation of the ether by hydrogenolysis; these disadvantages obviously make such a process completely ineffective.

SUMMARY OF THE INVENTION

Hence the object of the invention is to obtain a hydrogenation process not suffering from the above-mentioned disadvantages. It involves hydrogenating the cut in the presence of a bimetallic catalyst comprising at least one first noble metal from group VIII, such as palladium, rhodium, iridium and/or platinum, associated with at least one second metal, different from the first one and consisting of gold and (or) platinum. As a matter of fact, it has been found that said bimetallic catalysts are clearly more active and, in addition, do not result in any degradation of the desired ethers.

The proportion of the first metal (or the first metals) is usually from 0.05 to 2% by weight; the proportion of the second metal (or second metals) is usually from 0.05 to 2% by weight.

The catalyst used in the process according to the invention may be prepared in any suitable manner, for example by impregnating an inorganic carrier with an aqueous or organic solution of compounds of the metals to be deposited. These compounds may be inorganic salts or organic complexes such as, for minerals, the chlorides or nitrates and, for organic complexes, acetyl acetonates, for example. The impregnation of the two metals may be performed in one or two steps with, between the two optional steps, in intermediary roasting treatment and (or) reducing treatment. After the one or more impregnation steps, the catalyst may be roasted in air and then reduced in any convenient manner so as to bring it to its active form. The inorganic carrier will be preferably inert in order to avoid polymerization reactions; a convenient carrier would be for example, alumina or silica.

In a non limitative way, the hydrogenation may be performed in a tubular reactor wherein is placed the catalyst bed. The hydrogenation conditions will be selected in accordance with the type of olefin to hydrogenate, the desired conversion rate and the sulfur compound content of the charge. Hence they cannot be defined as priori in a precise manner. However they consist most generally of a temperature ranging from 20° to 300° C., a pressure ranging from 1 to 100 bars and a hourly space velocity of the charge (VVH) ranging from 0.5 to 10.

The charges to be treated contain for example 0–500 ppm by weight of sulfur, typically 1–300 ppm, for example 5–50 ppm. The ether may optionally be the only organic compound admixed with the olefin and may amount, for example, to 0.1–99.9% of the "olefin+ether" mixture.

The following examples are given to illustrate the invention but must not be considered as limiting the scope thereof.

EXAMPLES

Preparation of the catalysts

The catalyst carrier consists of balls of 2–4 mm diameter, having a specific surface of 70 $m^2/g$ and a total pore volume of 0.6 cc/g.

This carrier is used to prepare several catalysts containing nickel, palladium, rhodium, iridium and platinum, by dry impregnation of the carrier with aqueous solutions respectively containing nickel nitrate, palladium nitrate, rhodium trichloride, hexachloroiridic acid and hexachloroplatinic acid. The so-obtained catalysts are dried at 200° C. for 2 hours and then roasted in an air stream for 2 hours at 450° C. They are then charged into a tubular reactor and reduced under a hydrogen stream at atmospheric pressure for 12 hours.

The various prepared catalysts, their metal content by weight, as well as the reduction temperatures are summarized in Table I.

TABLE I

| CATALYST | METAL | % by weight | REDUCTION TEMPERATURE °C. |
|---|---|---|---|
| A | Ni | 10 | 400 |
| B | Pd | 0.3 | 100 |
| C | Rh | 0.3 | 300 |
| D | Ir | 0.3 | 300 |
| E | Pt | 0.3 | 300 |

Another series of bimetallic catalysts is prepared with the same carrier as above. The following metal pairs are used: Pd-Au, Pd-Pt, Rh-Au, Rh-Pt, Ir-Au, Ir-Pt and Pt-Au. As in example 1, the dry impregnation is performed with aqueous solutions containing the two dissolved salts. As salts, palladium nitrate, trichloroauric acid, hexachloroplatinic acid, rhodium trichloride and hexachloroiridic acid are used. The so-prepared catalysts, their metal composition by weight and the reduction temperature are summarized in Table II.

TABLE II

| CATALYSTS | metals % by weight | Reduction temp. °C. |
|---|---|---|
| F | 0.2 Pd—0.2 Au | 150 |
| G | 0.2 Rh—0.2 Au | 300 |
| H | 0.2 Pt—0.2 Au | 300 |
| I | 0.2 Ir—0.2 Au | 300 |
| J | 0.2 Pd—0.2 Pt | 150 |
| K | 0.2 Rh—0.2 Pt | 300 |
| L | 0.2 Ir—0.2 Pt | 300 |

EXAMPLE 1

The charge is a $C_5$ cut originating from a steam-cracking unit and already subjected to a selective hydrogenation of the diolefins contained therein. Its composition is given in Table III.

TABLE III

| HYDROCARBONS | % by weight |
|---|---|
| Isoprene | 0.1 |
| 2-methyl-1-butene + 2-methyl-2-butene | 25.2 |
| n-olefins | 15.2 |
| Cyclopentene | 11 |
| Saturated hydrocarbons | 48.5 |
| Sulfur | 11 ppm |

The $C_5$ cut is etherified with methanol in two successive reactors operating in liquid phase; the first reactor is of the type with a catalyst bed maintained expanded by an upward flow of reactants, with recycling of a portion of the effluent to the reactor input. The second reactor is of the fixed bed type. In the two reactors, the catalyst is a macroporous sulfonic resin (Amberlyst 15) as grains of 0.4 to 1 mm. Such a technique has been disclosed, for example, in the French patent No. 2,440,931. The average temperature is 72° C. in the first reactor and 55° C. in the second reactor. The ratio of methanol to the sum "methyl-1-butene+methyl-2-butene" is 1.3.

The composition and the main characteristics of the product obtained after etherification are given in Table IV below.

TABLE IV

| COMPOSITION | % by weight |
|---|---|
| Saturated hydrocarbons | 42.2 |
| Total olefins | 29.2 |
| Tert-amyl-methyl-ether (TAME) | 22.7 |
| methanol | 5.9 |
| Sulfur | 11 ppm |
| Bromine number | 67 |
| MON clear (Motor octane number without lead) | 85 |

The catalysts whose preparation has been described above are then used to hydrogenate said cut. The operation is conducted in the tubular reactor previously used for the catalyst prereduction. The charge is introduced in the presence of hydrogen in the following conditions:
pressure: 30 bars
temperature: 110° C.
V.V.H: 4
$H_2$/charge: 1 mole/mole.

After 100 hours, the reaction product is analyzed. The main characteristics obtained with the different monometallic and bimetallic catalysts are summarized in Table V.

It is apparent that bimetallic catalysts provide products of much lower olefins content and of substantially higher Motor octane number.

TABLE V

| CATALYSTS | TOTAL OLEFINS % | BROMINE NUMBER | MON |
|---|---|---|---|
| A | 25.3 | 58 | 85.0 |
| B | 10.3 | 24 | 85.3 |
| C Monometallic | 12.5 | 29 | 85.0 |
| D | 11.2 | 26 | 85.3 |
| E | 10.5 | 25 | 85.3 |
| F | 3.5 | 8 | 86.3 |
| G | 3.1 | 7 | 86 5 |
| H | 3.8 | 9 | 86.2 |
| I Bimetallic | 4.0 | 9 | 86.2 |
| J | 4.7 | 11 | 86.1 |
| K | 5.1 | 12 | 86.0 |
| L | 5.6 | 13 | 85.9 |

EXAMPLE 2

This example concerns the treatment of an ethyl ether cut containing as impurity 4 ppm of sulfur and 0.9% by weight of olefins, mainly as an methyl-butenes. The object is to obtain a purified ether containing less than 20 ppm of olefins. The hydrogenation is performed in the same reactor as in example 1, in the following conditions:
pressure: 30 bars
temperature: 100° C.
V.V.H: 2
$H_2$/charge: 1 mole/mole After 100 hours of operation, the produced ether is analyzed. The results are summarized in the following table:

| CATALYSTS | OLEFINS ppm IN THE PRODUCT |
|---|---|
| B (monometallic) | 300 |
| F (bimetallic) | <20 |
| G (bimetallic) | <20 |
| H (bimetallic) | <20 |
| I (bimetallic) | <20 |

| CATALYSTS | OLEFINS ppm IN THE PRODUCT |
| --- | --- |
| J (bimetallic) | <20 |
| K (bimetallic) | <20 |
| L (bimetallic) | <20 |

It is observed that, in contrast to the monometallic catalyst, the catalysts according to the invention provide ethyl ether complying with the required specification. Also with the use of bimetallic catalysts, the yield of produced ether with respect to the charged ether has been measured: this yield is 99.95%, thus showing, within the range of possible experimental errors, that no degradation of the ether takes place.

EXAMPLE 3

This example relates to the treatment of an ethyl ether cut containing less than 0.5 ppm of sulfur and 1.7% by weight of olefins (mainly methyl-butenes and n-pentenes). As in example 2, the object is to obtain a purified ether containing less than 20 ppm of olefins. The hydrogenation is performed in the same reactor as in example 1 in the following conditions:
pressure: 5 bars
temperature: 30° C.
V.V.H: 5
$H_2$/charge: 1 mole/mole After 100 hours of run, the produced ether is analyzed and the results are summarized in the following table:

| CATALYSTS | OLEFINS ppm IN THE PRODUCT |
| --- | --- |
| B (monometallic) | 190 |
| F (bimetallic) | <20 |
| G (bimetallic) | <20 |
| H (bimetallic) | <20 |
| I (bimetallic) | <20 |
| J (bimetallic) | <20 |
| K (bimetallic) | <20 |
| L (bimetallic) | <20 |

It appears that the required specification is achieved with bimetallic catalysts, but not with the monometallic catalyst.

What is claimed as the invention is:

1. In a process for purifying an olefin-containing ether mixture, said process comprising reacting said mixture with hydrogen in the presence of catalyst containing a noble metal, the improvement wherein the catalyst contains:
   (a) at least one noble metal selected from the group consisting of palladium, rhodium, iridium and platinum;
   (b) at least one metal different from (a), selected from the group consisting of gold and platinum;
   and wherein the reaction is conducted at a temperature of 20°–300° C., a pressure of 1–100 bar and with a space velocity of the mixture of 0.5–10 so as to increase the extent of hydrogenation of the olefin as compared to said process employing component (a) alone.

2. In a process for purifying an olefin-containing ether mixture, said process comprising reacting said mixture with hydrogen in the presence of catalyst containing a noble metal, the improvement wherein the catalyst contains:
   (a) at least one noble metal selected from the group consisting of palladium, rhodium, iridium and platinum, and
   (b) at least one metal different from (a), selected from the group consisting of gold and platinum;
   and wherein the reaction is conducted at a temperature of 20°–300° C., a pressure of 1–100 bar and at an hourly space velocity of the mixture of 0.5–10 wherein, in the catalyst, (a) is not palladium when (b) is gold.

3. In a process for purifying an olefin-containing ether mixture, said process comprising reacting said mixture with hydrogen in the presence of a catalyst containing a noble metal, the improvement wherein the catalyst contains:
   (a) at least one noble metal selected from the group consisting of palladium, rhodium, iridium and platinum;
   (b) at least one metal different from (a), selected from the group consisting of gold and platinum so as to increase the extent of hydrogenation of the olefin as compared to said process employing component (a) alone.

4. A process according to claim 3, wherein the catalyst comprises a carrier, a first metal (a) in a proportion by weight of 0.05 to 2% and a second metal (b) in a proportion by weight from 0.05 to 2%.

5. A process according to claim 4, wherein the carrier is alumina or silica.

6. In a process for purifying an olefin-containing ether mixture, said process comprising reacting said mixture with hydrogen in the presence of a catalyst containing a noble metal, the improvement wherein the catalyst contains:
   (a) at least one noble metal selected from the group consisting of palladium, rhodium, iridium and platinum, and
   (b) at least one metal different from (a), selected from the group consisting of gold and platinum wherein, in the catalyst, (a) is not palladium when (b) is gold.

* * * * *